United States Patent [19]

McCarthy

[11] Patent Number: 4,590,181

[45] Date of Patent: May 20, 1986

[54] SYNTHETIC IMMUNOREGULATORS AND METHODS OF USE AND PREPARATION

[75] Inventor: Robert E. McCarthy, Omaha, Nebr.

[73] Assignee: Board of Regents of the University of Nebraska, Lincoln, Nebr.

[21] Appl. No.: 451,016

[22] Filed: Dec. 20, 1982

[51] Int. Cl.$^4$ .................. A61K 31/715; A61K 39/12; C07H 1/00; C08B 37/02
[52] U.S. Cl. ........................................ 514/54; 424/89; 536/1.1; 536/112
[58] Field of Search .................. 536/1.1, 112; 424/88, 424/89, 180, 91, 92

[56] References Cited

U.S. PATENT DOCUMENTS 4,359,458  11/1982  Nair et al. ............................ 536/1.1
4,372,883   2/1983  Matuhashi et al. ............... 424/91 X

OTHER PUBLICATIONS

McCarthy et al. *Immunology*, 32:963, 1977.

Primary Examiner—Christine M. Nucker
Assistant Examiner—Shawn P. Foley
Attorney, Agent, or Firm—Vincent L. Carney

[57] ABSTRACT

To regulate the immune response to an antigen, a subject is injected with the antigen and a polyanionic polysaccharide derivative having a molecular weight of between 10,000 and 600,000 selected to correspond to the antigen. For virus, as an example, mycodextran sulfate or pustulan sulfate may be used in sufficient quantities to stimulate cell-mediated immune responses without stimulating synthesis of gamma E globulin and gamma G globulin. The polyanionic polysaccharide may be injected along to stimulate cell-mediated immune responses to antigens in a diseased subject.

4 Claims, No Drawings

SYNTHETIC IMMUNOREGULATORS AND METHODS OF USE AND PREPARATION

BACKGROUND OF THE INVENTION

This invention relates to immunoregulators and their methods of use and preparation.

It is known to use synthetic adjuvants or immunoregulators. However, the selection of such adjuvants was experimental and not based on sound theoretical principles because several factors necessary for such selection were not understood, such as: (1) the exact mechanism for the immune response; (2) if T-cells or B-cells or both T-cells and B-cells were involved; (3) the manner in which adjuvants interact with the immune system for a specific response; and (4) the manner in which compounds or mixtures can be synthesized to enable them to elicit the desired response.

A prior art synthetic adjuvant, dextran sulfate, has a polysaccharide molecule with anionic groups attached. The use of dextran sulfate as an adjuvant was disclosed in McCarthy, R. E., Arnold, L. W., and Babcock, G. F.: "Dextran Sulfate: An Adjuvant for Cell-Mediated Immune Responses," *Immunology*, 32:963, 1977. The immune response is based upon trial and error and it was not known if it would stimulate a T-cell response without a B-cell response.

Thus, prior art techniques and adjuvants have had several disadvantages, such as: (1) they are not predictable except by trial and error; (2) new adjuvants cannot be easily discovered or synthesized; (3) it is difficult to know the best manner and time of using them; and (4) they are not usable to elicit only certain responses such as to select one that stimulates a T-cell reponse but does not stimulate antibody synthesis.

SUMMARY OF THE INVENTION

Accordingly, it is an object of this invention to provide novel synthetic immunoregulators.

It is a further object of the invention to provide a novel technique for obtaining, using and preparing synthetic immunoregulators.

It is a still further object of the invention to provide a novel technique for the use of synthetic immunoregulators to study specific immune reactions.

It is a still further object of the invention to provide a novel method for immunizing patients or animals.

It is a still further object of the invention to provide a novel method for using synthetic immunoregulators to regulate immune responses.

It is a still further object of the invention to provide a novel technique for enhancing cell-mediated immune responses without stimulating the synthesis of gamma-E globulin or gamma-G globulin.

It is a still further object of the invention to provide a novel technique for enhancing cell-mediated immune responses with reduced probability of anaphylactic shock reactions.

It is a still further object of the invention to provide a novel technique for specifically enhancing cell-mediated immune responses without simultaneously stimulating synthesis of immune globulin G and immune globulin E.

It is a still further object of the invention to provide a novel technique for utilizing an adjuvant that selectively regulates only one of the actions of T-cells or B-cells in immunology.

It is a still further object of the invention to provide a novel technique for utilizing an adjuvant that is incorporated into a viral vaccine so as to minimize anaphylactic shock reactions.

It is a still further object of the invention to provide a novel method synthesizing immunoregulators by substituting chemical anionic groups onto a high-molecular-weight backbone of a compound that is not strongly antigenic to selectively arrive at an adjuvant which causes a predetermined stimulating response.

It is a still further object of the invention to provide a novel technique for selecting certain derivatives of polysaccharide compounds which affect the humoral and cellular immune responses in a predetermined manner.

It is a still further object of the invention to provide a novel technique for controlling the humoral hemagglutinating antibody responses (IgM and IgG) of animals and the responses of the classes of immunoglobulin E and $G_1$ which are associated with anaphylactic reactions.

It is a still further object of the invention to provide a novel technique for synthesizing compounds to cause specific immunoregulatory effects.

It is a still further object of the invention to provide novel high-molecular-weight sulfate compounds which have known immunoregulatory effects.

In accordance with the above and further objects of the invention, the immune response of a subject is regulated by an injection of an antigen and a synthetic immunoregulator in sufficient amount to provide a selected type and degree of immune response in the subject. The synthetic immunoregulator includes a high-molecular-weight compound which is not by itself strongly antigenic with groups on it that interact with specific lymphocytes. The high-molecular-weight compound may be a polysaccharide and the interacting groups may be polyanionic groups, such as sulfate. The polysaccharide should be sulfated to provide at least two sulfate sites.

As can be understood from the above summary, the immunoregulators of this invention and its methods of use and preparation have several advantages, such as: (1) they can be used for T-cell-mediated responses only and thus avoid anaphylactic shock; (2) specific synthetic adjuvants are available to operate in a predictable manner; (3) it is possible to use a dosage and adjuvant for a known type of response; and (4) it is possible to synthesize adjuvants for particular antigens.

SPECIFIC DESCRIPTION

Broadly, a novel adjuvant is provided which stimulates a specific immune response without stimulating other unnecessary immune responses and thus reduces undesirable effects that might be caused by the administration of the immune dose. The adjuvant is administered in conjunction with the administration of an antigen or by itself to stimulate the immune response to an antigen already in the subject such as cancer cells.

In one embodiment, adjuvants enhance cell-mediated immune responses without stimulating synthesis of gamma-E globulin and gamma-G globulin. Since the cell-mediated immune responses are the effective mechanisms against viral diseases and the gamma-G globulin and the gamma-E globulin classes of immunoglobulin cause anaphylactic shock reactions, the adjuvant increases the effectiveness of immune injections against viruses without creating shock effects.

To prepare the adjuvant, certain active groups and high-molecular-weight compounds which are not strongly antigenic are selected and the groups attached to convert the high-molecular-weight compound from an immunologically inert compound to a compound that exerts regulatory effects on the immune response system. For example, polyanionic groups on polysaccharides having molecular weights of between 10,000 and 600,000 have been shown to stimulate T-cells selectively. Sulfation of such high-molecular-weight compounds has provided effective adjuvants. The resulting adjuvant has an effect that reflects both the high-molecular-weight backbone and the nature and the amount of the attached group and the selection is made to achieve a desired result taking all three of these factors into consideration.

Polysaccharides which are either inert when tested in their unsulfated condition or which produce minimal immunological response changes are active immunoregulators following sulfation. The degree of sulfation can be modulated so that: (1) some compounds have saturation of all available sites that accept the sulfate; and (2) some compounds have partial sulfation. When modulated, complete sulfation results in the greatest immunoregulatory effect while moderate sulfation yields a lesser immunoregulatory effect.

The polysaccharide sulfate derivatives stimulate cell-mediated T-cell-dependent immune responses without stimulating antibody-mediated immune responses that are B-cell dependent. Certain unmodified polysaccharides stimulate only B-cells and other materials are known which under certain conditions stimulate B-cell and T-cell responses to different degrees. Consequently, the proper approach may be selected and used according to the needs of the subject under certain circumstances.

Cell-mediated immune stimulation increases as the number of sites for each unit of backbone molecule that is bound to an anionic group increases without an increase in B-cell stimulation. For purposes of this discussion: (1) T-cell response is a delayed sensitivity reaction of more than ten percent of a control no sooner than four hours after challenge and usually 18 to 24 hours after challenge; and (2) B-cell response is a sensitivity reaction earlier than or four hours after challenge that is more than ten percent of a control.

Two compounds which provide an adequately large molecular backbone for formation into a selective T-cell adjuvant are mycodextran and pustulan. Mycodextran consists of a polymer of D-glucosyl residues with alternating alpha (1–4) and alpha (1–3) linkages, a product obtained by precipitation with alcohol from cultures of *Aspergillus japonicus* in a manner known in the art. Pustulan consists of D-glucosyl residues with beta (1–6) linkages, obtained from umbilicaria, papullosa, in a manner known in the art and sold by Calbiochem Corporation of San Diego, Calif.

The invention is illustrated by the following examples:

EXAMPLES

GENERAL

Two different basic polysaccharide backbone molecules were selected for use which varied in the degree of rigidity of the molecule. Two different anionic groups for binding and four control compounds were selected. The polysaccharides are mycodextran and pustulan and the anionic groups were acetyl and sulfate.

For each polysaccharide backbone, acetyl or sulfate groups were attached. The degree of sulfation was modulated in such a way that the compounds were tested with: (1) saturation of all available sites that accept the sulfate or (2) with partial sulfation.

Two methods of sulfation of the polysaccharides were used. Both involved the DMF-SO$_3$ complex. In one method the complex was prepared first and added to the polysaccharide suspended in DMF as described by R. G. Schweiger, *Carb. Res.* 21 (1972) 219–228. In the other method liquid SO$_3$ was added slowly (Sulfan B) to a cooled suspension of the polysaccharide in DMF. Product isolation is also different from that described by Schweiger in that a dialysis step was added and the product was obtained by lyophilization. A similar method was used for acylation.

Three strains of mice were used for all studies except one done on one strain of rats as a control. The strains of mice are: (1) B6D2F1/J (Jackson Laboratories, Bar Harbor, Me.); (2) CFW (Charles River, Wilmington, Mass.); and (3) ESP (Eppley Cancer Institute, Omaha, Nebr.). The strain of rats is COBS COF. On day seven, blood was collected by bleeding from the retroorbital venous plexus.

Candidate immunoregulators were evaluated by the footpad swelling assay. The antigen used was sheep red blood cells (SRBC) obtained from Colorado Serum Company in Denver Colo. The SRBC were washed three times in Hank's balanced salt solution (HBBS) and resuspended to a concentration of ten percent of the volume of SRBC in HBBS (volume-to-volume percentage). The immunoregulators were dissolved in HBBS and mixed with an equal volume of the SRBC to give a final concentration of five percent SRBC and the desired concentration of the immunoregulator.

The control group of mice were sensitized subcutaneously (s.c.) with five percent SRBC, whereas the experimental group received five percent SRBC and the appropriate concentration of the immunoregulator. All the solutions were made just prior to sensitization. In the event that the immunoregulators were lytic for SRBC, they were injected uncombined at the same site one after the other at the same time, the immunoregulator being administered first.

Blood was collected by retroorbital venous puncture on days seven and fifteen post sensitization and the mice were challenged in the footpads with 0.05 ml of twenty percent SRBC (in HBSS). The right footpad received the SRBC suspension; the left footpad received an equal amount of phosphate-buffered saline. The thickness of the footpads was measured at 4, 24 and 48 hours after challenge. The difference between the left and right footpads of each mouse was expressed as a percentage. The average percent footpad swelling (APFS) for each group of mice was determined by dividing the sum of the individual swellings by the number of mice in the group. The average percentage increase (API) was determined by subtracting the APFS of the control group from the APFS of the treated group.

The following steps were followed in this procedure:

1. Adjuvant compounds

The polysaccharide-compound adjuvants are: (1) mycodextran; (2) sulfated mycodextran; (3) pustulan; (4) sulfated pustulan; and (5) acylated pustulan.

2. Toxicity studies

Preliminary toxicity studies were performed to determine concentration of the adjuvants which can be tolerated by the mice. Only doses of adjuvants which do not exhibit systemic or local toxic effects were used in the assays. Four groups of five mice each were injected with a range of doses of candidate adjuvants and observed for seven days for gross toxic effects. Animals were sacrificed, autopsied and examined for localized toxic effects.

3. Immediate and delayed hypersensitivity reactions

Mice were immunized with sheep red blood cells (SRBC) with or without adjuvants. Mice were sensitized on day zero subcutaneously in the scruff of the neck. Groups of ten mice each were injected with two doses of adjuvant compound and 0.02 milliliter per gram (ml/g) body weight of five percent SRBC in a carrier, or in other words five percent of the total volume of SRBC and carrier in volume of SRBC added (v/v). Control mice received only the SRBC. Mice of both sexes were used.

The blood from mice of the same group was pooled and the serum used to determine hemagglutinin titers. On day eight, the mice were challenged in the right hind footpad with 0.05 milliliter (ml) of a twenty percent (v/v) suspension of SRBC in phosphate-buffered saline (PBS) and in the left hind footpad with 0.05 ml of PBS only. The thickness of the footpads was measured at four, twenty-four and forty-eight hours with Vernier calipers after challenge. Bleeding and challenge were repeated on days fifteen and sixteen, respectively.

The difference in thickness between the left and right footpads of each mouse was expressed as a percentage. The average percent footpad swelling (APFS) for each group of mice was determined by dividing the sum of the individual swellings by the number of mice in the group. Significance was determined using the Student's t-test at ninety-five percent confidence limits as described by G. W. Snedecor and W. G. Cochran, 1967, *Statistical Methods,* Iowa State University Press, Ames, Iowa.

Positive footpad swellings occurring at four hours are immediate-type hypersensitivity reactions (antibody-mediated). Positive reactions occurring at twenty-four and forty-eight hours are delayed-type hypersensitivity reactions (cell-mediated).

4. Hemagglutinin titers

Antibody responses of the IgM and IgG classes against SRBC in immunized mice were determined using the microtiter method. All tests were performed in V-bottom microtiter plates (Cooke Engineering Co., Alexandria, Virginia). Twofold dilutions of sera (obtained as described above) were made in bovine serum albumin saline (BSA) (100 mg in 100 ml PBS). The titer was considered to be the reciprocal of the highest dilution showing positive agglutination.

5. Study of IgG$_1$ and IgE responses

Two types of experiments were conducted to study the responses of immunoglobulin associated with anaphylactic shock reactions. The first of these is active systemic anaphylaxis, which detects both IgG$_1$ and IgE simultaneously, and the second one is passive cutaneous anaphylaxis, which allows a determination of the presence or absence and relative concentrations of IgG$_1$ and IgE in animals that respond.

6. Active systemic anaphylaxis

Groups of ten mice were immunized subcutaneously on day zero with fifty micrograms of ovalbumin with or without the candidate adjuvant Two doses of adjuvant were used and a third group received antigen only. On day fourteen the mice were challenged intravenously with one milligram of ovalbumin and observed for four hours. The number of mice dying within this time was recorded and the percent of anaphylactic shock determined as the number of deaths divided by the number challenged. This protocol and dosage of antigen has been shown to result in predominantly IgE responses in mice. There is, however, some IgG$_1$ produced.

7. Passive cutaneous anaphylaxis (PCA)

Groups of ten mice were immunized with ovalbumin and the candidate adjuvant. The mice were bled from the retroobital venous plexus fourteen days following immunization. The sera were titrated for IgG$_1$ and IgE levels using PCA reactions at two and forty-eight hours, respectively, following intradermal injection of serum. Mice were challenged intravenously on day eighteen with one milligram of ovalbumin to assess systemic active anaphylaxis.

EXAMPLE 1

NON-ACYLATED PUSTULAN

The dosage of pustulan was determined in toxicity studies as described under the heading "2. Toxicity studies" above and the dosage was selected to be one hundred milligrams per kilogram of body weight of the mice. Three strains of mice were used, as shown in Table 1, five male and five female of each strain.

The immediate- and delayed-type hypersensitivity reactions were determined as described under the heading "3. Immediate and delayed hypersensitivity reactions" above. The results are shown in Table 1, in which a "0" (zero) indicates that the footpad swelling was less than ten percent over the control, a "+" (plus) sign means that there was significant footpad swelling greater than ten percent over the control and a "−" (minus) sign means there was a significant suppression of footpad swelling greater than ten percent over the control.

TABLE 1

| NON-ACYLATED PUSTULAN (used at 100 mg/kg body weight) | | | | | | |
|---|---|---|---|---|---|---|
| | | First Challenge | | | Second Challenge | |
| Strain | Sex | 4 hr | 24 hr | 48 hr | 4 hr | 24 hr | 48 hr |
| ESP | M | 0 | + | 0 | 0 | 0 | + |
| ESP | F | 0 | + | + | + | + | + |
| CFW | M | 0 | + | 0 | 0 | 0 | 0 |
| CFW | F | 0 | 0 | 0 | 0 | + | 0 |
| B6D2F1 | M | 0 | + | + | + | + | 0 |
| B6D2F1 | F | Strain Not Available Presently | | | | | |
| Hemagglutinin Titers: Significant Increase | | | | | | | |

The hemagglutinin titers were determined using the procedure described under the heading "4. Hemagglutinin titers." The results are shown in Table 1.

EXAMPLE 2

ACYLATED PUSTULAN

The dosage of acylated pustulan was determined in toxicity studies as described under the heading "2. Toxicity studies" above and the dosage was selected to be one hundred milligrams per kilogram of body weight of the mice. Three strains of mice were used, as shown in Table 2, five male and five female of each strain.

The immediate and delayed hypersensitivity reactions were determined as described under the heading "3. Immediate and delayed hypersensitivity reactions" above. The results are shown in Table 2,

TABLE 2

| | | ACYLATED PUSTULAN (used at 100 mg/kg body weight) | | | | | |
|---|---|---|---|---|---|---|---|
| | | First Challenge | | | Second Challenge | | |
| Strain | Sex | 4 hr | 24 hr | 48 hr | 4 hr | 24 hr | 48 hr |
| ESP | M | 0 | + | + | 0 | 0 | 0 |
| ESP | F | 0 | + | + | 0 | + | 0 |
| CFW | M | 0 | + | 0 | 0 | + | 0 |
| CFW | F | + | + | 0 | + | + | 0 |
| B6D2F1 | M | 0 | + | + | + | + | 0 |
| B6D2F1 | F | 0 | 0 | + | 0 | + | 0 |

Hemagglutinin Titers: Not Significant in which a "0" (zero) indicates that the footpad swelling was less than ten percent over the control, a "+" (plus sign) means that there was significant footpad swelling greater than ten percent over the control and a "−" (minus sign) means there was a significant suppression of footpad swelling greater than ten percent over the control.

The hemagglutinin titers were determined using the procedure described under the heading "4. Hemagglutinin titers." The results are shown in Table 2.

EXAMPLE 3

PUSTULAN SULFATE

The dosage of pustulan sulfate was determined in toxicity studies as described under the heading "2. Toxicity studies" above and the dosage was selected to be fifty milligrams per kilogram of body weight of the mice. Three strains of mice were used, as shown in Table 3, five male and five female of each strain.

The immediate and delayed hypersensitivity reactions were determined as described under the heading "3. Immediate and delayed hypersensitivity reactions" above. The results are shown in Table 3, in which a "0" (zero) indicates that the footpad swelling was less than ten percent over the control, a "+" (plus sign) means that there was significant footpad swelling greater than ten percent over the control and a "−" (minus sign) means there was a significant suppression of footpad swelling greater than ten percent over the control.

The hemagglutinin titers were determined using the procedure described under the heading "4. Hemagglutinin titers." The results are shown in Table 3.

TABLE 3

| | | PUSTULAN SULFATE (used at 50 mg/kg body weight) | | | | | |
|---|---|---|---|---|---|---|---|
| | | First Challenge | | | Second Challenge | | |
| Strain | Sex | 4 hr | 24 hr | 48 hr | 4 hr | 24 hr | 48 hr |
| ESP | M | 0 | + | + | + | + | + |
| ESP | F | 0 | + | + | 0 | + | + |
| CFW | M | 0 | 0 | + | 0 | + | + |
| CFW | F | + | + | + | 0 | + | 0 |
| B6D2F1 | M | − | + | 0 | + | + | 0 |
| B6D2F1 | F | 0 | + | + | 0 | + | 0 |

Hemagglutinin Titers: Significant Increase

Groups of ten mice were immunized subcutaneously with fifty micrograms of ovalbumin for each kilogram of body weight, with each group being a different of the three species and five of each group being male and five female. A control group was given only the ovalbumin at a dose of forty micrograms for each kilogram of body weight and the experimental group has given pustulan sulfate at a dose of one hundred micrograms per kilogram of body weight, following procedure 6 above under the heading "6. Active systemic anaphylaxis." The results are shown in Table 4.

EXAMPLE 4

MYCODEXTRAN

The dosage of mycodextran was determined in toxicity studies as described under the heading "2. Toxicity studies" above and the dosage was selected to be fifty milligrams per kilogram of body weight of the mice. Three strains of mice were used, as shown in Table 5, five male and five female of each strain.

TABLE 4

| OVALBUMIN-INDUCED ANAPHYLACTIC SHOCK Effect of Pustulan Sulfate on Anaphylactic Shock in Mice Percent Survivors | | | | | |
|---|---|---|---|---|---|
| ESP | | CFW | | B6D2F1 | |
| Male | Female | Male | Female | Male | Female |
| Control Group Given Ovalbumin Only | | | | | |
| 90 | 70 | 0 | 80 | 100 | 100 |
| (9/10) | (7/10) | (0/10) | (8/10) | (10/10) | (10/10) |
| Experimental Group Given Ovalbumin Plus Pustulan Sulfate | | | | | |
| 10 | 40 | 30 | 20 | 100 | 100 |
| (1/10) | (4/10) | (3/10) | (2/10) | (10/10) | (10/10) |

The immediate and delayed hypersensitivity reactions were determined as described under the heading "3. Immediate and delayed hypersensitivity reactions" above. The results are shown in Table 5, in which a "0" (zero) indicates that the footpad swelling was less ten percent over the control, a "+" (plus sign) means that there was significant footpad swelling greater than ten percent over the control and a "−" (minus sign) means there was a significant suppression of footpad swelling greater than ten percent over the control.

The hemagglutinin titers in Table 5 were determined using the procedure described under the heading "4. Hemagglutinin titers."

EXAMPLE 5

MYCODEXTRAN SULFATE

TABLE 5

| | | MYCODEXTRAN | | | | | |
|---|---|---|---|---|---|---|---|
| | | First Challenge | | | Second Challenge | | |
| Strain | Sex | 4 hr | 24 hr | 48 hr | 4 hr | 24 hr | 48 hr |
| ESP | M | 0 | + | 0 | 0 | 0 | 0 |
| ESP | F | 0 | + | 0 | 0 | 0 | 0 |
| CFW | M | + | 0 | 0 | 0 | 0 | 0 |
| CFW | F | 0 | 0 | + | 0 | + | + |
| B6D2F1 | M | + | 0 | + | + | + | + |
| B6D2F1 | F | − | + | 0 | 0 | 0 | + |

Hemagglutinin Titers: Not Significant

"2. Toxicity studies" above and the dosage was selected to be fifty milligrams per kilogram of body weight of mice. Three strains of mice were used, as shown in Table 6, five male and five female of each strain.

The immediate and delayed hypersensitivity reactions were determined as described under the heading "3. Immediate and delayed hypersensitivity reactions" above. The results are shown in Table 6, in which a "0" (zero) indicates that the footpad swelling was less than ten percent over the control, a "+" (plus sign) means that there was significant footpad swelling greater than ten percent over the control and a "−" (minus sign) means there was a significant suppression of footpad swelling greater than ten percent over the control.

The hemagglutinin titers were determined using the procedure described under the heading "4. Hemagglutinin titers." The results are shown in Table 6.

TABLE 6

MYCODEXTRAN SULFATE

| Strain | Sex | First Challenge | | | Second Challenge | | |
|---|---|---|---|---|---|---|---|
| | | 4 hr | 24 hr | 48 hr | 4 hr | 24 hr | 48 hr |
| ESP | M | 0 | + | + | 0 | + | 0 |
| ESP | F | 0 | + | + | 0 | + | 0 |
| CFW | M | 0 | + | 0 | + | + | + |
| CFW | F | 0 | + | + | + | + | 0 |
| B6D2F1 | M | 0 | + | + | 0 | + | 0 |
| B6D2F1 | F | + | + | + | 0 | + | 0 |

Hemagglutinin Titers: Not Significant

Groups of ten mice were immunized subcutaneously with fifty micrograms of ovalbumin, with each group being a different of the three species and five of each group being male and five female. A control group was given only the ovalbumin at a dose of forty milligrams per kilogram of body weight and the experimental group was given mycodextran sulfate at a dose of fifty milligrams per kilogram of body weight, following procedure 6 above under the heading "6. Active systemic anaphylaxis." The results are shown in Table 7. Similar groups of ten mice were immunized with ovalbumin and an adjuvant and bled from the retroorbital venous plexus, following procedure 7 under the heading "7. Passive cutaneous anaphylaxis (PCA)" above, to determine systemic active anaphylaxis. The results are shown in Table 7.

EXAMPLE
MYCODEXTRAN SULFATE IN RATS

TABLE 7

OVALBUMIN-INDUCED ANAPHYLACTIC SHOCK
Effect of Mycodextran Sulfate on Anaphylaxis in Mice

| Percent Survivors | | | | | |
|---|---|---|---|---|---|
| ESP | | CFW | | B6D2F1 | |
| Male | Female | Male | Female | Male | Female |
| Control Group Given Ovalbumin Only | | | | | |
| 70 | 100 | 100 | 100 | 100 | 100 |
| (7/10) | (10/10) | (10/10) | (10/10) | (10/10) | (10/10) |
| Experimental Group Given Ovalbumin Plus Mycodextran | | | | | |
| 60 | 70 | 0 | 0 | 100 | 100 |
| (6/10) | (7/10) | (0/10) | (0/10) | (10/10) | (10/10) |

The dosage of mycodextran sulfate was determined in toxicity studies as described under the heading "2. Toxicity studies" above and the dosage was selected to be fifty milligrams per kilogram of body weight of the rats. The strain of rats used is as shown in Table 8, five male and five female rats were used.

The immediate and delayed hypersensitivity reactions were determined as described under the heading "3. Immediate and delayed hypersensitivity reactions" above. The results are shown in Table 8, in which a "0" (zero) indicates that the footpad swelling was less than ten percent over the control, a "+" (plus sign) means that there was significant footpad swelling greater than ten percent over the control and a "−" (minus sign) means there was a significant suppression of footpad swelling greater than ten percent over the control.

The hemagglutinin titers were determined using the procedure described under the heading "4. Hemagglutinin titers." The results are shown in Table 8.

TABLE 8

MYCODEXTRAN EXPERIMENTS IN RATS
MYCODEXTRAN SULFATE

| Strain | Sex | First Challenge | | |
|---|---|---|---|---|
| | | 4 hr | 24 hr | 48 hr |
| COBS CDF | M | 0 | + | 0 |
| COBS CDF | F | 0 | + | 0 |

Hemagglutinin Titers: Significant Increase in Male and Female Rats

EXAMPLE 7

PUSTULAN SULFATE

The dosage of pustulan sulfate was determined in toxicity studies as described under the heading "2. Toxicity studies" above and the dosage was selected to be fifty milligrams per kilogram of body weight of the mice. Three strains of mice were used, as shown in Tables 9-14, five male and five female of each strain.

The immediate and delayed hypersensitivity reactions were determined as described under the heading "3. Immediate and delayed hypersensitivity reactions" above. The results are shown in Tables 9-14, in which a "0" (zero) indicates that the footpad swelling was less than ten percent over the control, a "+" (plus sign) means that there was significant footpad swelling greater than ten percent over the control and a "−" (minus sign) means there was a significant suppression of footpad swelling greater than ten percent over the control.

The hemagglutinin titers were determined using the procedure described under the heading, "4. Hemagglutinin titers". The results are shown in Table 15.

TABLE 9

| | | Hypersensitivity Immediate Type | | |
|---|---|---|---|---|
| Strain | Sex | Adjuvant Effect | No Effect | Suppress Effect |
| ESP | M | | x | |
| ESP | F | | x | |
| CFW | M | | x | |
| CFW | F | x slight | | |
| B6D2F1/J | M | | | x slight |
| B6D2F1/J | F | x | | |

TABLE 10

| | | Hypersensitivity Immediate Type | | |
|---|---|---|---|---|
| Strain | Sex | Adjuvant Effect | No Effect | Suppress Effect |
| ESP | M | x | | |
| ESP | F | | x | |
| CFW | M | | x | |
| CFW | F | | x | |
| B6D2F1/J | M | x | | x |
| B6D2F1/J | F | | | x |

TABLE 11

| | | Hypersensitivity 24-Hr Delayed Type | | |
|---|---|---|---|---|
| Strain | Sex | Adjuvant Effect | No Effect | Suppress Effect |
| ESP | M | x | | |

TABLE 11-continued

| Strain | Sex | Hypersensitivity 24-Hr Delayed Type | | |
|---|---|---|---|---|
| | | Adjuvant Effect | No Effect | Suppress Effect |
| ESP | F | x | | |
| CFW | M | | x | |
| CFW | F | x | | |
| B6D2F1/J | M | x | | |
| B6D2F1/J | F | x | | |

TABLE 12

| Strain | Sex | Hypersensitivity 24-Hr Delayed Type | | |
|---|---|---|---|---|
| | | Adjuvant Effect | No Effect | Suppress Effect |
| ESP | M | x | | |
| ESP | F | x | | |
| CFW | M | x | | |
| CFW | F | x | | |
| B6D2F1/J | M | | | |
| B6D2F1/J | F | x | | |

TABLE 13

| Strain | Sex | Hypersensitivity 48-Hr Delayed Type | | |
|---|---|---|---|---|
| | | Adjuvant Effect | No Effect | Suppress Effect |
| ESP | M | x | | |
| ESP | F | x | | |
| CFW | M | x | | |
| CFW | F | x | | |
| B6D2F1/J | M | | x | |
| B6D2F1/J | F | x | | |

TABLE 14

| Strain | Sex | Hypersensitivity 48-Hr Delayed Type | | |
|---|---|---|---|---|
| | | Adjuvant Effect | No Effect | Suppress Effect |
| ESP | M | x | | |
| ESP | F | x | | |
| CFW | M | x | | |
| CFW | F | | | x |
| B6D2F1/J | M | | | x |
| B6D2F1/J | F | | | x |

TABLE 15
PUSTULAN SULFATE IN MICE

| Strain | Dosage | Hemagglutinin Titers | |
|---|---|---|---|
| | | Pre-Challenge | Post-Challenge |
| ESP | 50 mg/kg | 2 | 512 |
| ESP | Control | 0 | 256 |
| ESP | 50 mg/kg | 0 | 512 |
| ESP | Control | 2 | 256 |
| CFW | 50 mg/kg | 0 | 256 |
| CFW | Control | 2 | 32 |
| CFW | 50 mg/kg | 4 | 256 |
| CFW | Control | 4 | 256 |
| B6D2F1/J | 50 mg/kg | 2 | 512 |
| B6D2F1/J | Control | 2 | 128 |
| B6D2F1/J | 50 mg/kg | 2 | 512 |
| B6D2F1/J | Control | 2 | 128 |

For toxicity studies with pustulan at fifty, one hundred, two hundred or four hundred milligrams per kilogram of body weight, some local inflammation at the injection site is observed. For pustulan sulfate at twenty-five, fifty, one hundred or two hundred milligrams per kilogram of body weight, no toxicity is observed at twenty-five or fifty milligrams per kilogram of body weight but toxic effects and some deaths are observed in animals receiving one hundred or two hundred milligrams per kilogram of body weight.

In the delayed hypersensitivity response-footpad swelling test, the twenty-four- and forty-eight-hour delayed hypersensitivity responses with pustulan sulfate adjuvant are indicated in Tables 11–14. The results indicate that there was a response by five or six groups of animals at twenty-four and forty-eight hours after the first challenge. Following the second challenge, five of six groups of mice indicate a significant delayed hypersensitivity response.

There are some increases in titers of hemagglutinating antibodies in the animals receiving pustulan sulfate. The results are shown in Table 15. There were no deaths from anaphylactic shock in the groups of animals following the first challenge with antigen. Five of ten male ESP mice died following the second challenge. No signs of shock were observed in the remaining animals. Pustulan sulfate exerts significant adjuvant action in the system employed. The effect is greatest on the delayed hypersensitivity reaction. Changes in immunoglobulin synthesis are minimal.

Each of the classes of high-molecular-weight polysaccharides is either inert in its unsulfated condition or produces minimal immunological response changes and is an active immunoregulator following sulfation. In those instances in which the degree of sulfation is modulated in such a way that the compounds have all available sites saturated that accept the sulfate or with partial sulfation, complete sulfation results in the greatest immunoregulatory effect while moderate sulfation yields a lesser immunoregulatory effect.

The results of this study are summarized in Tables 1 through 15 and are consistent with the prior results of studies on dextran sulfate as reported by R. E. McCarthy, L. W. Arnold and G. F. Babcock in *Immunology*, 1977, 32, pp. 963–974, entitled "Dextran sulphate: an adjuvant for cell-mediated immune responses," the disclosure of which is incorporated herewith for reference.

Non-acylated pustulan, i.e., pustulan molecule with no substituent groups, has a certain degree of regulatory effect in that the delayed hypersensitivity footpad swelling response is increased significantly at twenty-four hours following both first and second challenges with antigen. Acylated pustulan, the form in which it occurs naturally, is seen to have a positive effect on the delayed footpad swelling reaction, which in general is greater than that observed for the unsubstituted pustulan molecule. Pustulan sulfate is observed to have an even greater effect on the immune response than either of the other two forms of pustulan. The effect of pustulan sulfate on anaphylactic shock reactions in mice is reported in Table 4.

The incidence of fatal anaphylaxis in ESP and CFW mice is greatly increased when pustulan sulfate is used as an adjuvant. The B6D2F1 strain of animal is extremely resistant to the induction of anaphylaxis under any circumstances and it has been our experience to date that no compound acts as an anaphylactic shock inducer in this strain.

The results of experiments with mycodextran are reported in Tables 5 through 8. Unsubstituted mycodextran has a minimal effect on the immune response as indicated by changes in footpad swelling reaction. Sulfation (Tables 6 and 7) converts this material into a highly active immunoregulator. Moreover, mycodextran sulfate has a significant effect on delayed hypersensitivity responses in rats as well (Table 8). The effect of mycodextran sulfate on anaphylaxis in mice is presented in Table 7. This compound has its greatest effect in CFW mice, in which there was one hundred percent lethality.

As can be understood from the above description, the immunoregulators of this invention and its methods of use and preparation have several advantages, such as: (1) it can be used for T-cell-mediated responses only and thus reduce anaphylactic shock; (2) specific synthetic adjuvants are available to operate in a predictable manner; (3) it is possible to use a dosage and adjuvant for a known type of response; and (4) it is possible to synthesize adjuvants for particular antigens.

Although a preferred embodiment has been described with some particularity, many modifications and variations may be made in the preferred embodiment without deviating from the invention. Accordingly, it is to be understood that, within the scope of the appended claims, the invention may be practiced other than as specifically described.

What is claimed is:

1. A composition adaptable for use as an injectable solution which comprises:
    a viral antigen and
    an adjuvant consisting essentially of a polysaccharide having a molecular weight from about 10,000 to 600,000 selected from the group consisting of pustulan and mycodextran wherein said polysaccharide has at least two anionic chemical groups attached thereto, which adjuvant stimulates a cell-mediated immune response to said viral antigen without stimulating other immune responses.

2. A composition according to claim 1 wherein said anionic chemical groups are selected from the group consisting of acetyl and sulfate.

3. A composition adaptable for use as an injectable solution which comprises: an adjuvant consisting essentially of a polysaccharide having a molecular weight from about 10,000 to 600,000 selected from the group consisting of pustulan and mycodextran wherein said polysaccharide has at least two anionic chemical groups attached thereto said anionic chemical groups being selected from the group consisting of acetyl and sulfate, which adjuvant stimulates a cell-mediated immune response without stimulating other immune responses.

4. A method of immunizing a subject against a viral antigen comprising innoculating the subject with a polysaccharide having a molecular weight between 10,000 and 600,000 selected from the group consisting of pustulan and mycodextran wherein said polysaccharide has at least two anionic chemical groups attached thereto, which adjuvant stimulates a cell-mediated immune response to said viral antigen without stimulating other immune respones.